United States Patent [19]
Jackson

[11] Patent Number: 5,836,890
[45] Date of Patent: Nov. 17, 1998

[54] APPARATUS AND METHOD OF PROVIDING A PERSONAL FERTILITY PREDICTOR

[75] Inventor: Joseph N. Jackson, 13621 Cerise Ave., No. 1, Hawthorne, Calif. 90250

[73] Assignee: Joseph N. Jackson, Hawthorne, Calif.

[21] Appl. No.: 865,506

[22] Filed: May 30, 1997

[51] Int. Cl.[6] .................................................. A61B 5/00
[52] U.S. Cl. ........................................................ 600/551
[58] Field of Search .................................. 600/551, 591, 600/549; 364/413.12

[56] References Cited

U.S. PATENT DOCUMENTS

| 5,043,888 | 8/1991 | Uriarte | 600/551 |
| 5,058,084 | 10/1991 | Riesen | 600/551 |
| 5,515,344 | 5/1996 | Ng | 600/551 |

*Primary Examiner*—Max Hindenburg
*Attorney, Agent, or Firm*—Blakely, Sokoloff, Taylor & Zafman

[57] ABSTRACT

The present invention is a method and apparatus of predicting fertility using a processor-based system. The apparatus comprises a housing and a control panel enclosed within the housing that has a plurality of function keys for entering information related to a fertility cycle. The apparatus further comprises a memory that stores instruction sequences and a processor coupled to the memory, for executing the stored instruction sequences. The stored instruction sequences include process steps to cause the processor to: (a) determine a first period in a predetermined month in which a menstrual cycle is in progress; (b) determine a second period of maximum chance of pregnancy chance of pregnancy in the predetermined month; (c) determine a third period in the predetermined month, of increased chance of pregnancy; (d) determine a fourth period of decreased chance of pregnancy in the predetermined month; (e) compute the first, the second, the third and the fourth periods for a predetermined number of following months. A display coupled to the processor, the memory and the control panel, displays the first, second, third and fourth periods of the predetermined month. The display is scrollable to display the first, second, third and fourth periods of the predetermined number of following months.

25 Claims, 8 Drawing Sheets

DECREASED CHANCE OF PREGNANCY

MENSTRUAL CYCLE IN PROGRESS

INCREASED CHANCE OF PREGNANCY

MAXIMUM CHANCE OF PREGNANCY

APPARATUS AND METHOD OF PROVIDING A PERSONAL FERTILITY PREDICTOR

BACKGROUND OF THE INVENTION

1. Field of the Invention

The present invention relates to personal information systems, and more particularly, to a method and apparatus of providing a personal fertility predictor.

2. Description of the Related Art

In 1990, the number of females that are of child bearing age exceeded 60 million. For this segment of the population, responsible gynecological monitoring and/or family planning can serve to enhance lifestyles and to facilitate the exercise of informed choice regarding conception and reproduction.

Although contraceptives are widely used, the contraceptive methods and devices currently available vary in ease of use, safety and effectiveness. One contraceptive technique, typically known as the natural family planning method, takes advantage of the fact that a woman is able to become pregnant only when ovulation occurs during the reproductive cycle. If this contraceptive technique is selected, a woman must either practice abstinence during ovulation or use a separate type of contraception during that period. For the rest of the cycle, she is unlikely to conceive. Conversely, for couples planning to start a family, conception will be most likely during the ovulation cycle and least likely during the rest of the cycle.

To implement this method of contraception, a woman must determine the time of ovulation and the pattern of her reproductive cycle. This involves precise monitoring of one's ovulation and menstrual cycles, precise record keeping, charting and numerous computations. Such computations are laborious, may be imprecise and projections are typically difficult to ascertain. Moreover, reference to these records or charts may be inconvenient.

Accordingly, there is a need in the art for a simple, elegant, and cost-effective method and apparatus for providing a personal fertility predictor that is safe, reliable and convenient to use.

BRIEF SUMMARY OF THE INVENTION

The present invention is a method and apparatus of predicting fertility using a processor-based system. The apparatus comprises a housing and a control panel enclosed within the housing that has a plurality of function keys for entering information related to a fertility cycle. The apparatus further comprises a memory that stores instruction sequences and a processor coupled to the memory, for executing the stored instruction sequences. The stored instruction sequences include process steps to cause the processor to: (a) determine a first period in a predetermined month in which a menstrual cycle is in progress; (b) determine a second period of maximum chance of pregnancy chance of pregnancy in the predetermined month; (c) determine a third period in the predetermined month, of increased chance of pregnancy; (d) determine a fourth period of decreased chance of pregnancy in the predetermined month; (e) compute the first, the second, the third and the fourth periods for a predetermined number of following months. A display coupled to the processor, the memory and the control panel, displays the first, second, third and fourth periods of the predetermined month. The display is scrollable to display the first, second, third and fourth periods of the predetermined number of following months.

BRIEF DESCRIPTION OF THE DRAWINGS

The features and advantages of the present invention will become more readily apparent to those ordinarily skilled in the art after reviewing the following detailed description and accompanying drawings, wherein.

DETAILED DESCRIPTION OF THE INVENTION

Figure 1:
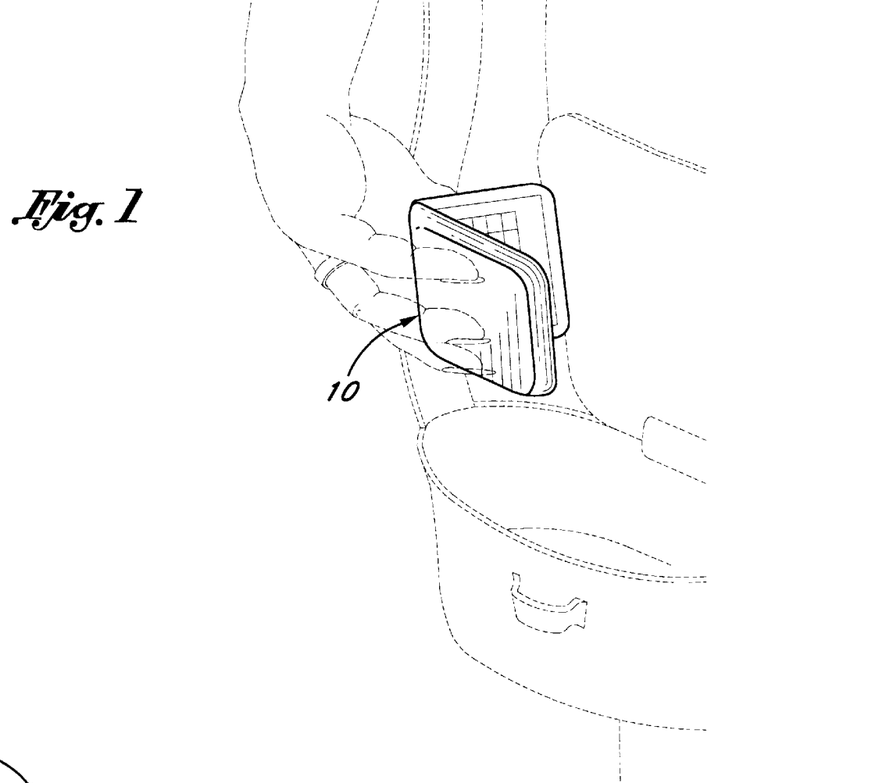
FIG. 1 is a perspective view of one embodiment of the personal fertility predictor of the present invention, being inserted into a purse by a user.

FIG. 1 is a perspective view of one embodiment of the personal fertility predictor of the present invention, being inserted into a purse by a user. In one embodiment, the personal fertility predictor 10 is 3 inches by 3 inches and resembles a powder compact. Such a design facilitates portability and discrete use of the personal fertility predictor 10. When not in use, the predictor 10 may be fitted securely and discretely in a purse, briefcase or pocket. The housing of the personal fertility predictor 10 may be made of plastic, metal or an alloy.

Figure 2A:
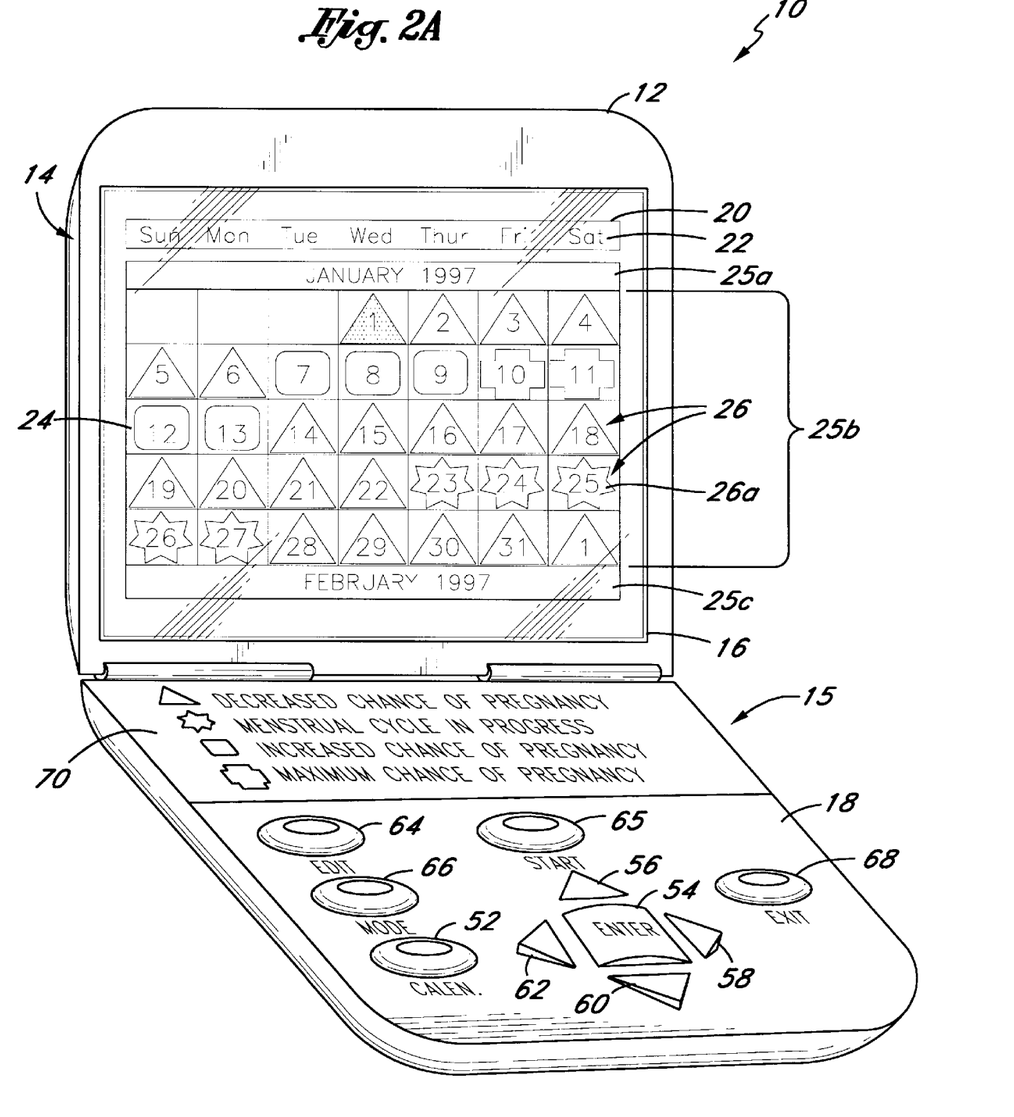
FIG. 2A is an enlarged perspective view of the personal fertility predictor of FIG. 1.

FIG. 2A is an enlarged perspective view of the personal fertility predictor 10 of FIG. 1. The personal fertility predictor 10 comprises a compact housing 12 which comprises an external cover 14 and an internal display portion 15 which comprises a display 16 and a control panel 18. In one embodiment, the display 16 is a Liquid Crystal Display (LCD). In another embodiment, the display 16 comprises a display panel 20 that has indicia 22 representing the days of the week and a display screen 24. The indicia may be provided as a decal or molded onto the display panel 20.

When activated, the display screen 24 displays a calendar matrix 25 having seven display lines, that provides calendar and personal fertility prediction information. In particular, the first display line 25a illustrates the current month and year; the second through sixth display lines (collectively referred to as 25b) each displays corresponding to personal fertility within a particular week of the current month. The final display line 25a illustrates the following month and year. In one embodiment, the second through sixth display lines 25b are further divided into seven columns, each of which corresponds to a particular day of the week. In this embodiment, there are 35 display sections, each of which will be referred to herein as display section 26. The current day of the month in calendar matrix 25 will be highlighted.

In one preferred embodiment, each display section 26 includes a number representing the day of the month, and a background pattern 26a which represents one of four periods within a reproductive cycle of the user: (a) a period in which the woman's menstrual cycle is in progress; (b) a period of maximum chance of pregnancy; (c) a period of increased chances of pregnancy; and (d) a period of decreased chance of pregnancy. The background pattern 26a may take the form of various geometrical shapes, such as triangles, squares, stars and crosses. Alternatively, the background pattern 26a may take the form of different colors. In one embodiment, as shown in FIG. 2A, the display sections 26 having a background pattern 26a in the form of a cross represents a period of maximum chance of pregnancy for the individual whose fertility cycle is being display. The display sections 26 having a background pattern 26a in the form of a square represents a period of increased chance of pregnancy; the display sections 26 having a background pattern 26a in the form of a triangle represents a period of decreased chance of pregnancy; and the display sections 26 having a background pattern 26a in the form of a star represents a period in which the individual's menstrual cycle is in progress.

Figure 2B:
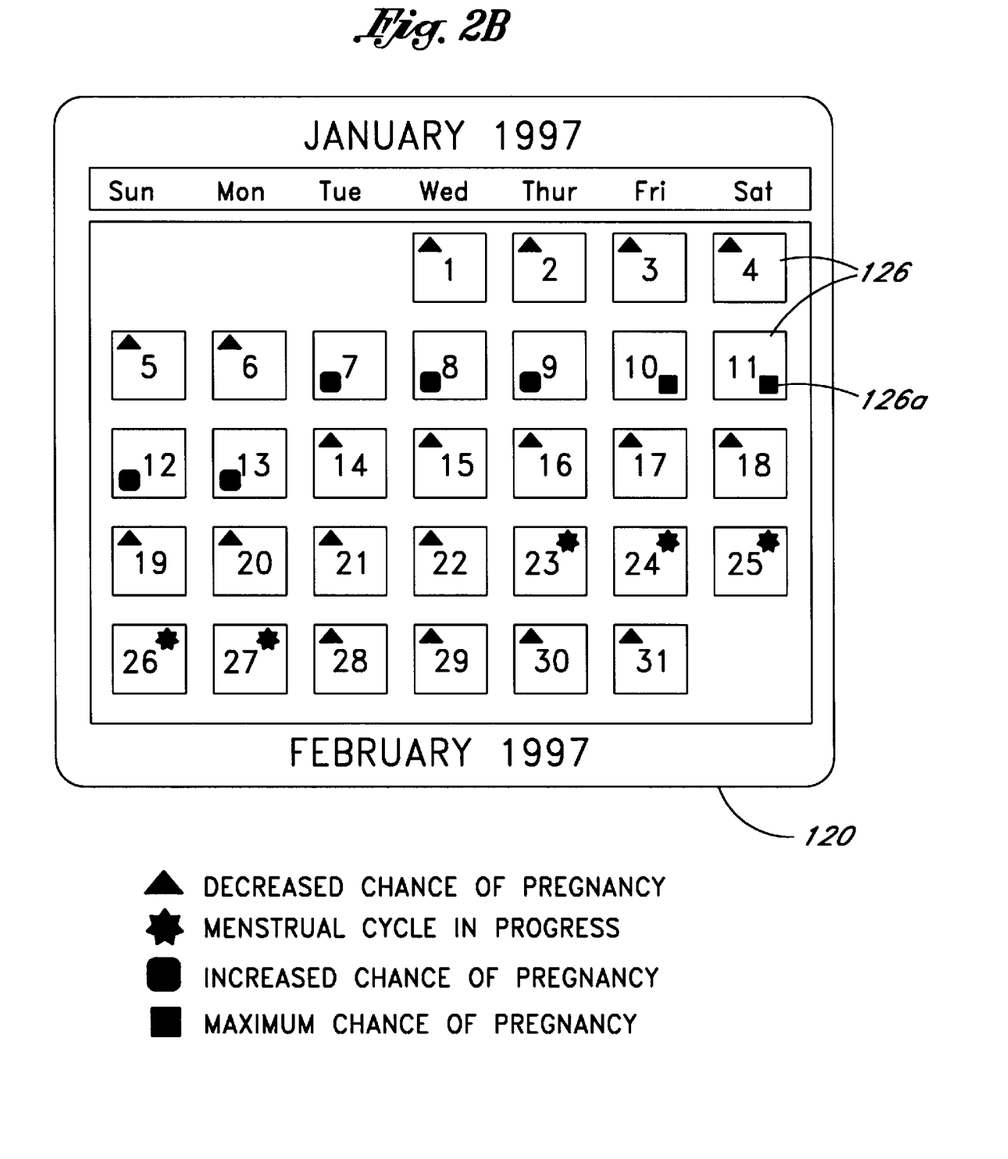
FIG. 2B illustrates a second embodiment of the display panel 20 of FIG. 2A.

FIG. 2B illustrates a second embodiment of the display panel 20 of FIG. 2A. In this embodiment, the display panel 120 has a plurality of display sections 126. Each display section 126 has a background pattern 126a with a plurality of geometric shapes, such as a triangle in the top left corner of the display section 126, a star in the top right corner of the display section 126, a square in the bottom right corner of the display section 126 and an oval in the bottom left corner of the display section. Each geometric shape represents one of four periods within a reproductive cycle. For example, the display sections 126 having a background pattern 126a in the form of an oval in the bottom left corner of the display section 126 represents a period of increased chance of pregnancy; the display sections 126 having a square in the bottom right corner of the display section 126 represents a period of maximum chance of pregnancy; the display sections 126 having a background pattern 126a in the form of a triangle in the top left corner of the display section 126 represents a period of decreased chance of pregnancy; the display sections 126 having a background pattern 126a in the form of a star in the top right corner of the display section 126 represents a period in which the individual's menstrual cycle is in progress. In one embodiment, all four indicia, namely, the start, the oval, the triangle and the square, all co-exist on each display section 126. However, only one of the four indicia, i.e. the appropriate indicia corresponding to a particular cycle, will be visible (i.e., will light up) at any particular time.

Figure 2C:
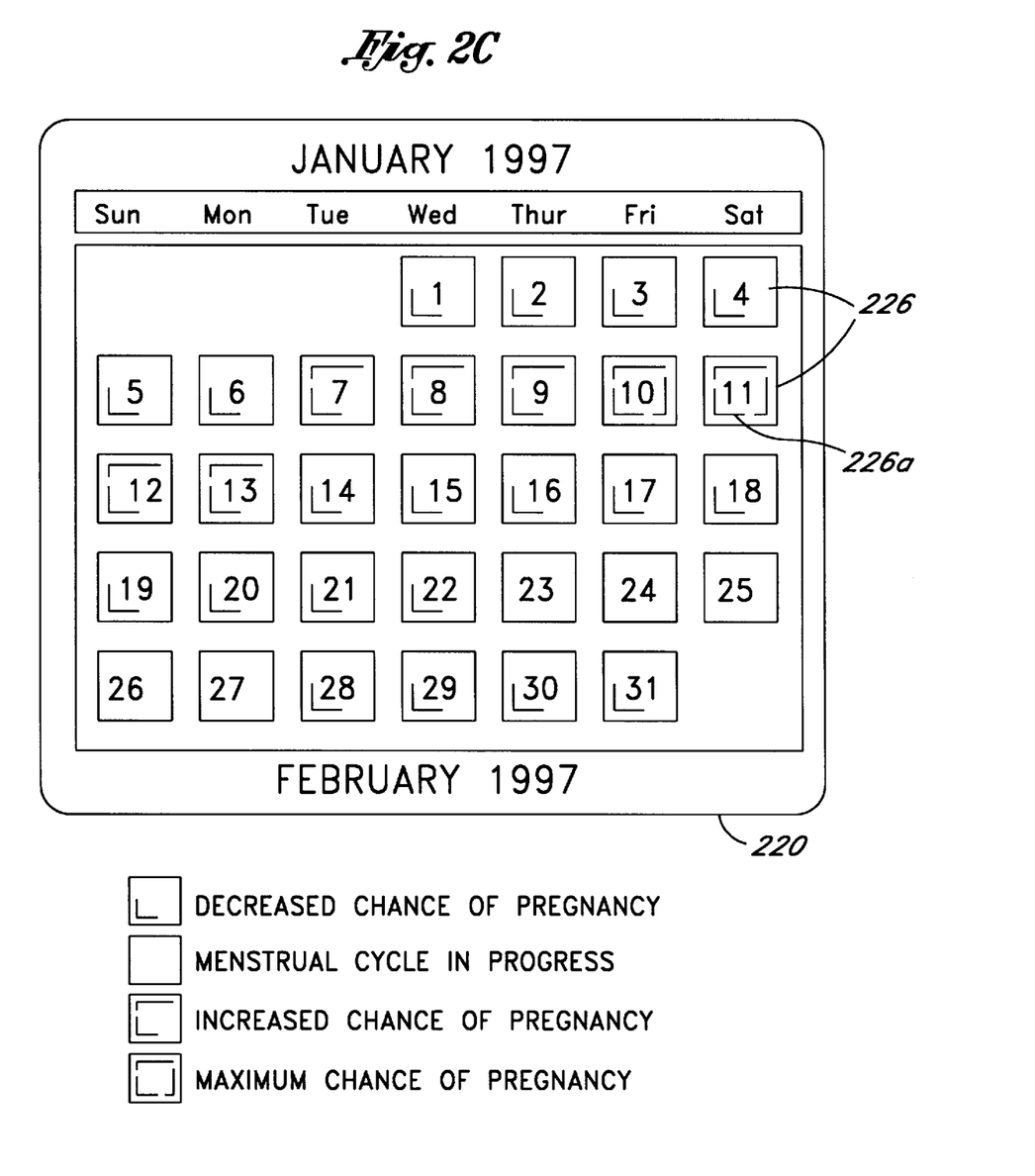
FIG. 2C illustrates a third embodiment of the display panel 20 of FIG. 2A.

FIG. 2C illustrates a third embodiment of the display panel 20 of FIG. 2A. In this embodiment, the display panel 220 has a plurality of display sections 226. The display sections 226 having a background pattern 226a in the form of a single L-shaped indicia represent a period of decreased chance of pregnancy; the display sections 226 having a background pattern 226a in the form of 2 L-shaped indicia represent a period of increased chance of pregnancy; the display sections 226 having a background pattern 226a in the form of 3 L-shaped indicia represent a period in which the individual's menstrual cycle is in progress, while the display sections 226 having no background pattern (i.e., no indicia) represent a period in which the individual's menstrual cycle is in progress. In one embodiment, all three L-shaped indicia co-exist on each display section 226. However, only the appropriate indicia (i.e., any one of: zero, one, two or three L-shaped indicia) corresponding to a particular cycle will be visible (i.e., will light up) at any particular time.

Figure 2D:
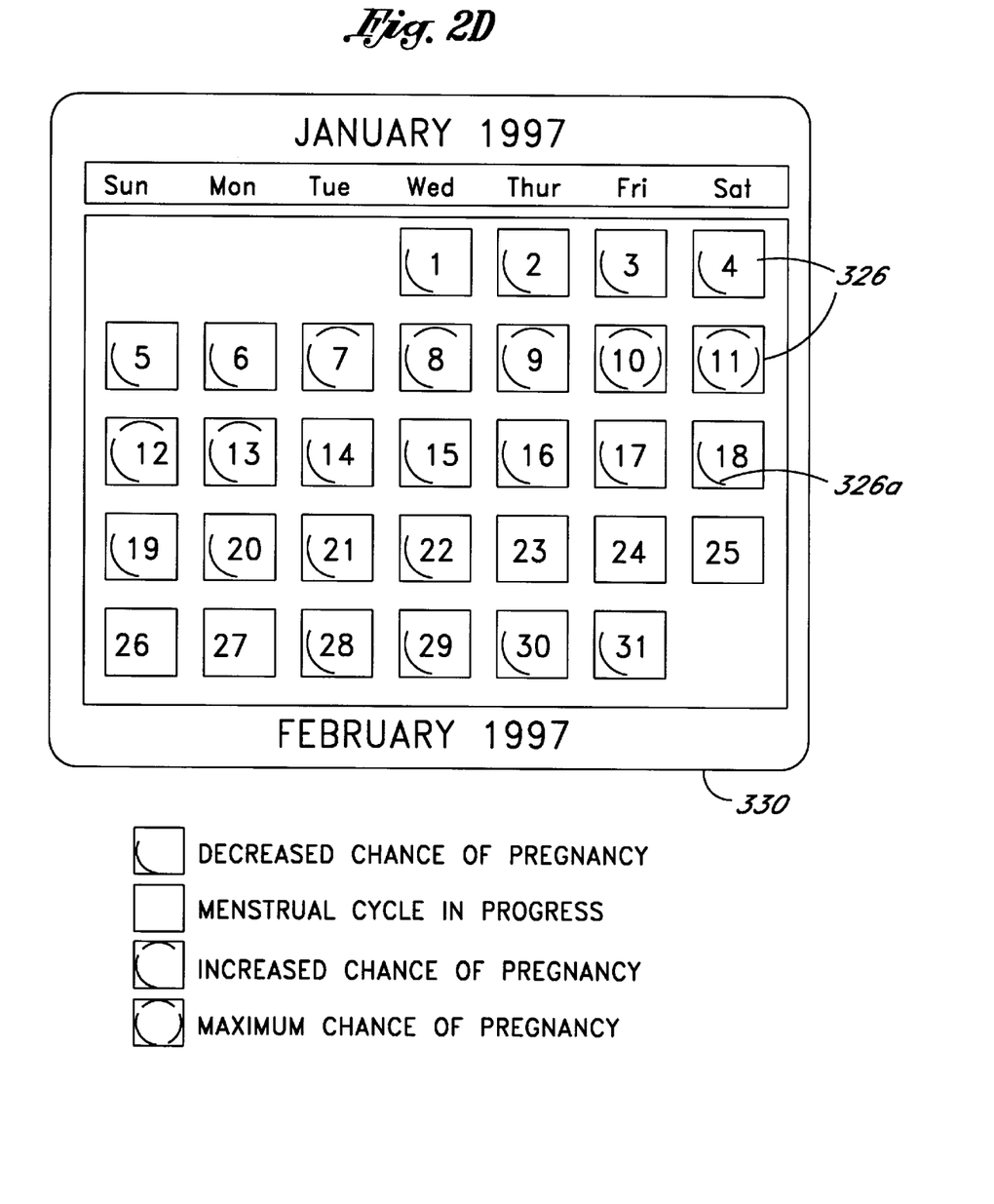
FIG. 2D illustrates a fourth embodiment of the display panel 20 of FIG. 2A.

FIG. 2D illustrates a fourth embodiment of the display panel 20 of FIG. 2A. In this embodiment, the display panel 320 has a plurality of display sections 326. The display sections 326 having a background pattern 326a in the form of an arc-shaped indicia represents a period of decreased chance of pregnancy; the display sections 326 having a background pattern 326a in the form of 2 arc-shaped indicia represent a period of increased chance of pregnancy; and the display section 326 having a background pattern 326a in the form of 3 arc-shaped indicia represent a period in which the individual's menstrual cycle is in progress; while the display sections 326 having no background pattern (i.e., no indicia) represent a period in which the individual's menstrual cycle is in progress. In one embodiment, all three arc-shaped indicia exist on each display section 326. However, only the appropriate indicia (i.e., any one of zero, one, two or three arc-shaped indicia) corresponding to a particular cycle will be visible (i.e., will light up) at any particular time.

The control panel 18 comprises a plurality of function keys which facilitate the input of information or commands. When ready for use, the operator may open the predictor 10 to enter data or commands through the control panel 18. In one embodiment, the control panel 18 comprises a CALEN or ON key 52, an ENTER key 54, a upward scroll key 56, a right scroll key 58, a downward scroll key 60 and a left scroll key 62. The control panel 18 further comprises an EDIT key 64. In an alternate embodiment, the control panel 18 also comprises a START key 65, a SET or MODE key 66, an EXIT key 68 and a HELP key. The control panel 18 also comprises a display portion 70 which provides a legend of the various cycles (a)–(d) that are displayed on the display screen 24.

Figure 3:
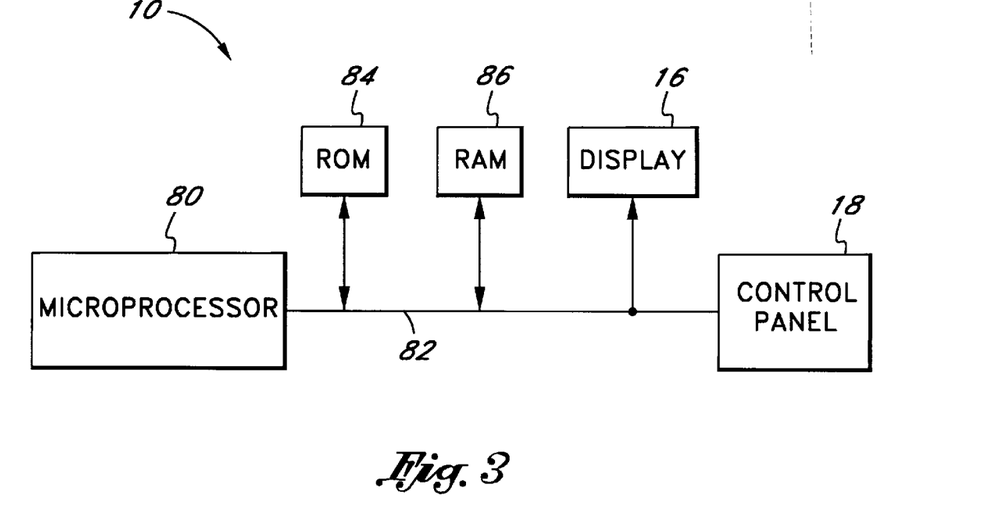
FIG. 3 is a block diagram of the personal fertility predictor of FIGS. 1 and 2A.

FIG. 3 is a block diagram of the personal fertility predictor of FIGS. 1 and 2. The personal fertility predictor 10 also comprises a microprocessor 80 that is coupled to the control panel 18 (FIG. 1) via an input/output (I/O) bus 82. A read only memory module (ROM) 84 and a random access memory module (RAM) 86 are each bidirectionally coupled to the microprocessor 80 via I/O bus 82. The display 16 (FIG. 1) is also coupled to the I/O bus 82.

Operation of the personal fertility predictor 10 will now be described with reference to FIGS. 1 and 2. To activate the predictor 10, the START key 65 is first depressed. In one alternate embodiment, the ENTER key 54 can be used in place of the START key 65 to initiate or start the personal fertility predictor 10. In this embodiment, the START key 65 will not be implemented. In response, the microprocessor 80 sends a command to the display 16 to prompt the user to enter the current time (including the hour and the minutes), day, month, and year. The entries may be made using the upward scroll key 56, the right scroll key 58, the downward scroll key 60 and/or the left scroll key 62. Upon selecting the appropriate time, day, month or year, the ENTER key 54 is depressed. The entered information is stored in RAM 86. In an alternate embodiment, the user may depress the SET or MODE key 66 so as to enter the current time.

In one embodiment, the microprocessor 80 also prompts the user, through the display 16, to enter a password. In this embodiment, the microprocessor 80 first displays the message "PLEASE ENTER PASSWORD", followed by the display of the calendar matrix 25. The user may enter a four-digit password using the numbers displayed on each display section 26. Selection of the numbers is made by scrolling up, down, left or right using the scroll keys 56, 58, 60 and/or 62. When the user encounters the desired number, as indicated by a highlighted background section, the ENTER key 54 is depressed. In an alternate embodiment, the user may depress the SET or MODE key 66 again so as to enter the password. It is apparent to one of ordinary skill in the art that a password of a greater number or a lesser number of digits may be used.

When the user if ready to input personal information, the SET or MODE key 66 is depressed. If this key is not available, the CALEN key 52 may be used. The microprocessor 80 responds by displaying a calendar matrix illustrating the days of the current month. Where applicable, a number of days from the previous month will precede the days of the current month. Likewise, where applicable, a number of days from the following month will follow the days of the current month. The user may then enter the days of her last menstrual cycle. This is accomplished by scrolling through the calendar matrix 25 using the left and/or right scroll keys 62 and/or 58 respectively. Upon encountering the first day of her last menstrual cycle, the ENTER key 54 is depressed. The user then uses the right scroll key 58 to proceed to the next day of her last menstrual cycle and selects that day by depressing the ENTER key 54. It is apparent to one of ordinary skill in the art that the user may also enter the days of her last menstrual cycle from the last day to the first day, i.e., by scrolling using the left scroll key 62. The EDIT key 64 may be used to edit the information entered. Upon completion of this task, the microprocessor 80 will store the entered information and compute the days corresponding to each of the four periods for a plurality of months.

If the user desires to review or reset any of the information entered during any of the previously described steps, she may depress the SET or MODE key 66 again. The microprocessor 80 responds by presenting each of the above described modes, such as the mode for or setting of the current time, the mode for entering or altering the password, the mode for entering the first and last day of the last menstrual cycle or the edit mode. Upon the presentation of each mode, the user may alter the previously entered information. Alternatively, the user may continue to depress the SET or MODE Key 66 until the appropriate mode is encountered. An EXIT key 68 may be optionally provided to facilitate the termination of the review process. If this key is not available, the SET or MODE key 66 may again be depressed to exit from the review process. In an alternate embodiment, the CALEN key 52 may be depressed to exit from the review process. In one embodiment, the predictor 10 will automatically shut off when no activity has been detected for 15 seconds. In an alternate embodiment, a HELP key (not shown) may be provided to enable the user to obtain assistance in using the predictor 10.

Once the personal information has been input, the user may utilize the fertility predictor 10 to obtain future information or past information regarding an individual's fertility cycles. To obtain such information, the user first depresses the CALEN key 52. The fertility predictor 10 responds by presenting a display panel 20, where a segment on the first display line 25a which typically displays the current month is configured to flash. This is a prompt for the user to enter the current month. The entry may be made by using the upward scroll key 56, the right scroll key 58, the downward scroll key 60 and/or the left scroll key 62. Once entered, the fertility predictor 10 prompts the user to enter the corresponding year. This is accomplished by flashing a segment on the first display line 25a which typically displays the current year. The entry may be made as discussed earlier. Once the desired month and year heave been entered, the ENTER key 54 is depressed. The microprocessor 80 then proceeds to compute the fertility cycle of the user corresponding to the entered month and year. In particular, four periods within the user's reproductive cycle will be displayed: (a) a period in which the woman's menstrual cycle is in progress; (b) a period of maximum chance of pregnancy; (c) a period of increased chances of pregnancy; and (d) a period of decreased chance of pregnancy. Once the computation is complete, the fertility predictor 10 displays the fertility information corresponding to the month and year specified. The user may obtain information for a preceding/following month or a plurality of preceding/following months by using the scroll keys 56, 60. In this manner, the user may use any future information displayed to plan vacations, weddings or honeymoons. Alternatively, the user may use any past information displayed to determine certain personal information such as date of conception.

Figure 4A:
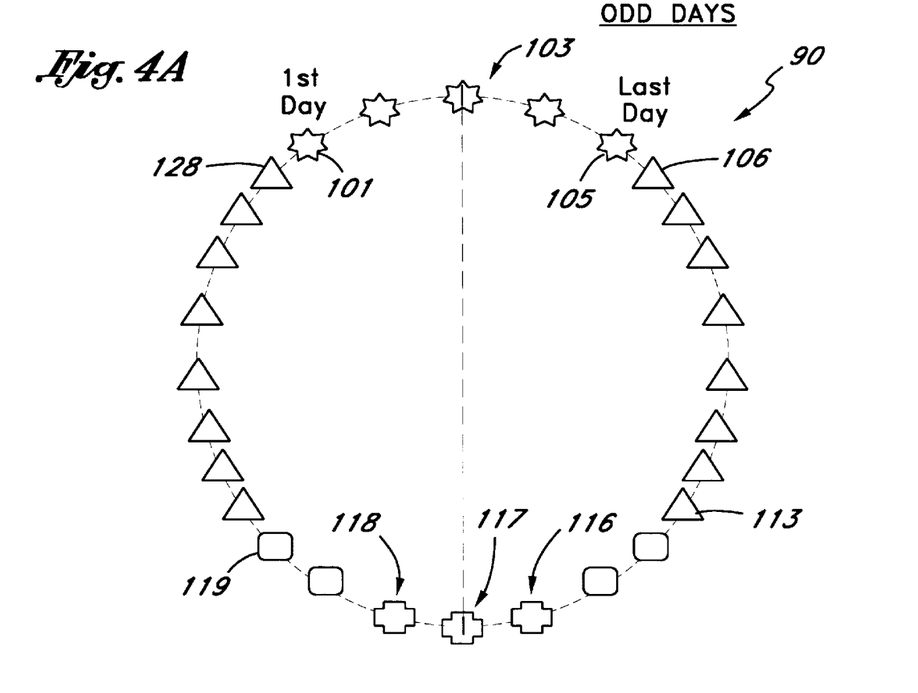
FIG. 4A illustrates a chart 90 that describes the fertility prediction process of the present invention, based on a menstrual cycle of odd days.

FIG. 4A illustrates a chart 90 that describes the fertility prediction process of the present invention, based on a menstrual cycle of odd days. The first and last days 100, 105 of an individual's menstrual cycle are first determined. Based on the first and last days, a middle day 103 of the menstrual cycle is determined. Assuming that the individual's fertility cycle is 28 days, the ovulation period for the individual is a 24-hour period that is exactly 14 days from the middle day 103 of the menstrual cycle, i.e., day 117. For reasons of precaution, the day 116 prior to or the day 118 following the ovulation period (day 117) is also considered as a day in which there is a maximum chance of pregnancy. Whichever day (day 117 or 118) is not selected as one in which there is a maximum chance of pregnancy is then considered a day in which there is an increased chance of pregnancy. The two days prior to (days 115 and 116) and following (days 119 and 120) this period are considered days in which there is an increased chance of pregnancy. The remaining days, i.e., days 106–113 (8 days) and 121–128 (8 days), are considered days in which there is a decreased chance of pregnancy.

Figure 4B:
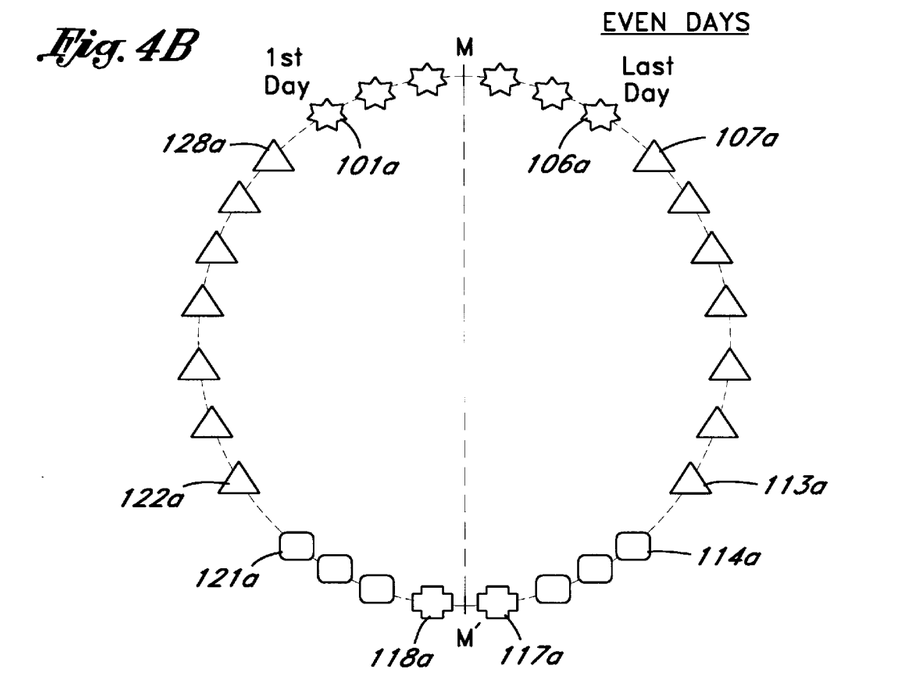
FIG. 4B illustrates a chart 90a that describes the fertility prediction process of the present invention, based on a menstrual cycle of even days.

FIG. 4B illustrates a chart 90a that describes the fertility prediction process of the present invention, based on a menstrual cycle of even days. The first and last days 100a, 106a of an individual's menstrual cycle are first determined. Based on the first and last days, a mid-section or interval M which occurs between the first and last days 100a and 106a of the menstrual cycle is determined. Assuming that the individual's fertility cycle is 28 days, the ovulation period for the individual is a 24-hour period that is exactly 14 days from M, i.e., at M'. For reasons of precaution, both days 117a and 118a are considered days in which there is a maximum chance of pregnancy. The three days prior to (days 114a and 116a) and following (days 119a and 121a) this period are considered days in which there is an increased chance of pregnancy. The remaining days, i.e., days 107a–113a (7 days) and 122a–128a (7 days), are considered days in which there is a decreased chance of pregnancy.

Figure 5:
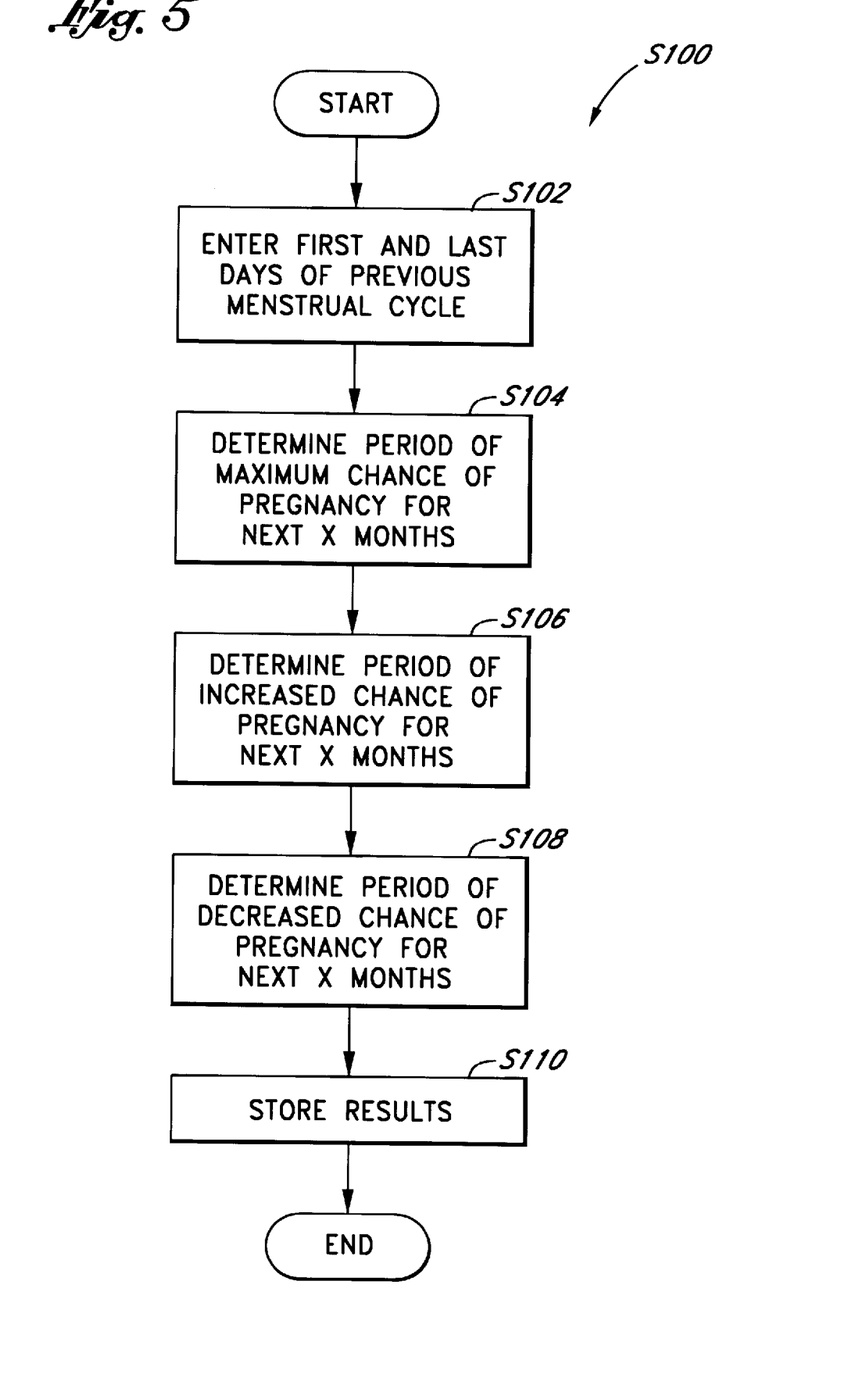
FIG. 5 is a flow chart of the process S100 of predicting fertility of the present invention.

FIG. 5 is a flow chart of the process S100 of the present invention. Beginning from a start state, the process S100 proceeds to process step S102, in which the user is prompted to enter the first and last days of a previous menstrual cycle. The process S100 then proceeds to process step S104, where it determines the period of maximum chance of pregnancy for the next predetermined number (or X) of months, based on the process shown in FIGS. 4A or 4B and the corresponding text. The process S100 then proceeds to process step S106, where it determines the periods of increased chance of pregnancy for the next X months. The process S100 then advances to process step S108, where it determines the periods of decreased chance of pregnancy for the next X months. The process S100 then stores the results, which may be retrieved for later reference. The process S100 then terminates.

Should the user determine that her fertility cycle has changed, or if the calculations based on earlier menstrual cycles are no longer valid, she may re-enter the first and last days of her menstrual cycle, so that the microprocessor 80 may recalculate the various periods of her fertility cycle.

Figure 6:
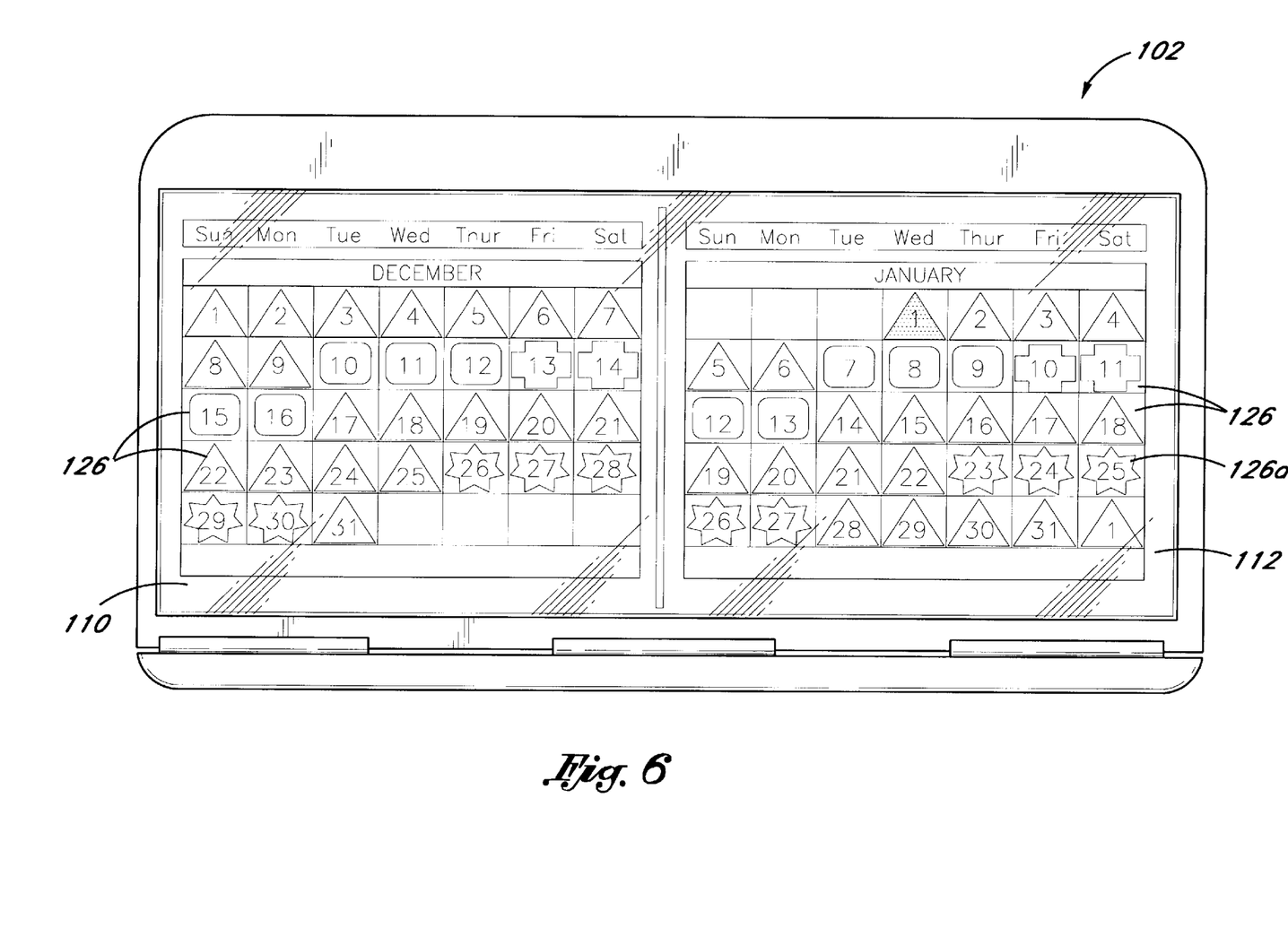
FIG. 6 illustrates an alternate embodiment of the personal fertility predictor of the present invention.

FIG. 6 illustrates the display screen of an alternate embodiment of the fertility predictor of the present invention. The alternate embodiment 100 of the fertility predictor may be implemented using a palmtop, laptop, notebook or desktop computer. The fertility predictor 100 comprises a display screen 102. When activated, the display screen 102 displays two calendar matrices 110 and 112; one of which is located on the left portion of the display screen, and the other of which is located on the right portion of the display screen 102. It is apparent to one of ordinary skill in the art that the calendar matrices 110 and 112 may also be configured so that one calendar matrix 110 is located above the other calendar matrix 112 on the display screen 102.

In a preferred embodiment, each calendar matrix 110 or 112 has seven display lines, that provides calendar and personal fertility prediction information. In particular, the first display line illustrates the days of the week; the second display line illustrates the current month and year; the third through seventh display lines each displays corresponding to personal fertility within a particular week of the current month. In one embodiment, the third through seventh display lines are further divided into seven columns, each of which corresponds to a particular day of the week. In this embodiment, there are 35 display sections, each of which will be referred to herein as display section 126. In another embodiment, the current month will be displayed on calendar matrix 112, while the previous month will be displayed on calendar matrix 110. The current day of the month in calendar matrix 112 will be highlighted.

As with the embodiment illustrated in FIG. 2, each display section 126 includes a number representing the day of the month, and a background pattern 126a which represents one of four periods within a reproductive cycle of the user: (a) a period of decreased chance of pregnancy; (b) a period in which the woman's menstrual cycle is in progress; (c) a period of increased chances of pregnancy; and (d) a period of maximum chance of pregnancy. The background pattern 126a may take the form of various geometrical shapes, such as triangles, squares, stars and crosses. Alternatively, the background pattern 126a may take the form of different colors. In one embodiment, as shown in FIG. 6, the display sections 126 having a background pattern 126a in the form of a cross represents a period of maximum chance of pregnancy for the individual whose fertility cycle is being display. The display sections 126 having a background pattern 126a in the form of a square represents a period of increased chance of pregnancy; the display sections 126 having a background pattern 126a in the form of a triangle represents a period of decreased chance of pregnancy; and the display sections 126 having a background pattern 126a in the form of a star represents a period in which the individual's menstrual cycle is in progress.

In this embodiment, the user may enter or alter information by scrolling leftwards, rightwards, upwards or downwards on each calendar matrix 110 or 112 by respectively using the left, right, up or down scroll keys that are available on the keyboard of the palmtop, laptop, notebook or desktop computer. By displaying fertility information for two consecutive months simultaneously, the fertility predictor 100 illustrated in FIG. 6 facilitates convenient review and entry of the user's fertility cycle.

The implementation of the present invention provides a simple, elegant and cost-effective method and apparatus for providing a personal fertility predictor that is safe, reliable and convenient to use.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. An apparatus for predicting fertility, comprising:
a housing;
a control panel enclosed within said housing, said control panel having a plurality of function keys for entering information related to a fertility cycle;
a memory that stores instruction sequences;
a processor coupled to said memory, for executing the stored instruction sequences;
wherein the stored instruction sequences include process steps to cause the processor to compute a chance of pregnancy for one of a first, second, third, and fourth periods in a predetermined month said first, second, third, and fourth periods corresponding to a menstrual cycle in progress, a maximum chance of preganancy, an increased chance of preganancy, and a decreased chance of pregnancy, respectively; and
a display coupled to said processor, said memory and said control panel, that displays a calendar showing days in said first, second, third and fourth periods of the predetermined month, each day being marked by one of a plurality of symbols to indicate said chance of pregnancy, said display being scrollable to display said first, second, third and fourth periods of the predetermined number of following months.

2. The apparatus of claim 1, wherein said display comprises a display screen and a display panel.

3. The apparatus of claim 2, wherein said display panel comprises a plurality of indicia, each representative of a day of the week.

4. The apparatus of claim 2, wherein said display screen comprises a plurality of display lines that displays fertility information related to said first, said second, said third and said fourth periods of a current month.

5. The apparatus of claim 4, wherein a first display line of said display screen displays indicia representative of a current month and a current year.

6. The apparatus of claim 4, wherein a predetermined number of said plurality of display lines displays indicia representative of said first, said second, said third and said fourth periods.

7. The apparatus of claim 2, wherein a last display line displays indicia representative of a following month and a year corresponding to said following month.

8. The apparatus of claim 1, wherein said control panel comprises an enter key for entering information, an upwards scroll key, a downwards scroll key, a left scroll key, and a right scroll key.

9. The apparatus of claim 8, wherein said control panel further comprises an edit key, an exit key and a help key.

10. The apparatus of claim 1, wherein said display screen turns off when activity has not been detected for a predetermined period.

11. A method for predicting fertility, the method comprising:

(a) entering information related to a fertility cycle;

(b) storing said information in a memory;

(c) computing a chance of preganancy based on said stored information, for one of a first, second, third, and fourth periods in a predetermined month, said first, second, third, and fourth periods corresponding to a menstrual cycle in progress, a maximum chance of preganancy, an increased chance of preganancy, and a decreased chance of pregnancy, respectively;

(d) computing said first, said second, said third and said fourth periods for a predetermined number of following months;

(e) displaying a calendar showing a days in said first, second, third and fourth periods of the predetermined month on a display; and (f) marking each day in said calendar by one of a plurality of symbols to indicate said chance of pregnancy.

12. The method of claim 11, wherein in (e), said display comprises a display screen and a display panel.

13. The method of claim 12, further comprising (g) scrolling the display screen to display said first, second, third and fourth periods of the predetermined number of following months.

14. The method of claim 12, further comprising turning off said display when activity has not been detected for a predetermined period.

15. The method of claim 11, wherein said first, second, third and fourth periods occur within a 28-day cycle.

16. The method of claim 11, wherein (c) comprises:

(c.1) determining a first and a last day of a menstrual cycle; and (c.2) providing a plurality of days beginning from the first day to the last day as the first period.

17. The method of claim 16, wherein (c) further comprises:

(c.3) determining a middle day of the first period;

(c.4) adding fourteen days to the middle day to provide a first day in the second period; and (c.5) providing the first day in the second period and a preceding day as the days in the second period.

18. The method of claim 17, wherein (c) further comprises:

(c.6) providing a period of three days following the second period and a period of two days prior to the second period as the third period.

19. The method of claim 16, wherein (c) further comprises:

(c.7) determining a middle day of the first period;

(c.8) adding fourteen days to the middle day to provide a first day in the second period; and (c.9) providing the first day in the second period and a following day as the days in the second period.

20. The method of claim 19, wherein (c) further comprises:

(c.10) providing a period of two days following the second period and a period of three days prior to the second period as the third period.

21. The method of claim 18, wherein (c) further comprises:

(c.11) providing a remaining number of days as the fourth period.

22. The method of claim 20, wherein (c) further comprises:

(c.12) providing a remaining number of days as the fourth period.

23. The method of claim 16, wherein (c) further comprises:

(c.3) determining a mid section of the first period;

(c.4) adding fourteen days to the middle day to provide a mid section of the second period; and (c.5) providing a day prior to the mid section of the second period and a day following the mid section of the second period as the days in the second period.

24. The method of claim 23, wherein (c) further comprises:

(c.6) providing a period of three days following the second period and a period of three days prior to the second period as the third period.

25. The method of claim 24, wherein (c) further comprises:

(c.7) providing a remaining number of days as the fourth period.

* * * * *